United States Patent
Mitra et al.

(10) Patent No.: US 6,391,286 B1
(45) Date of Patent: *May 21, 2002

(54) USE OF METALLOFLUOROCOMPLEXES FOR DENTAL COMPOSITIONS

(75) Inventors: Sumita B. Mitra, West St. Paul; Bing Wang, Woodbury, both of MN (US)

(73) Assignee: 3M Innovative Properties Company, Saint Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/560,331

(22) Filed: Nov. 17, 1995

(51) Int. Cl.$^7$ ................................................ A61K 7/22
(52) U.S. Cl. .......................... 424/54; 424/49; 424/53; 523/115; 523/116; 106/35
(58) Field of Search ................................ 523/116, 115; 424/49, 53, 54; 106/35

(56) References Cited

U.S. PATENT DOCUMENTS

| | | | | |
|---|---|---|---|---|
| 4,043,327 A | * | 8/1977 | Potter et al. ............... 128/89 R |
| 4,527,979 A | * | 7/1985 | McLean et al. ............. 433/128 |
| 4,808,228 A | * | 2/1989 | Ranoklev ..................... 106/35 |
| 4,832,745 A | | 5/1989 | Antonucci .................... 106/35 |
| 4,871,786 A | | 10/1989 | Aasen ........................ 523/113 |
| 4,872,936 A | | 10/1989 | Engelbrecht ............. 156/307.3 |
| 4,978,522 A | | 12/1990 | Barbera ....................... 424/52 |
| 5,130,347 A | | 7/1992 | Mitra ......................... 522/149 |
| 5,151,453 A | | 9/1992 | Ibsen et al. .................. 522/14 |
| 5,154,762 A | | 10/1992 | Mitra et al. .................. 106/35 |
| 5,204,398 A | * | 4/1993 | Cohen et al. ............... 523/116 |
| 5,218,070 A | | 6/1993 | Blackwell ................... 526/318 |
| 5,304,586 A | | 4/1994 | Hammesfahr et al. ...... 523/117 |
| 5,338,773 A | | 8/1994 | Lu et al. ..................... 523/116 |
| 5,367,002 A | * | 11/1994 | Huang et al. ............... 523/116 |
| 5,369,145 A | | 11/1994 | Gasman et al. ............. 523/120 |
| 5,411,584 A | | 5/1995 | Akinmade et al. ............ 106/35 |
| 5,472,991 A | * | 12/1995 | Schmitt et al. ............. 523/116 |
| 5,520,922 A | * | 5/1996 | Gasser et al. ............... 424/422 |
| 5,552,485 A | * | 9/1996 | Mitra et al. ................. 525/102 |

FOREIGN PATENT DOCUMENTS

| | | |
|---|---|---|
| CH | A 631 344 | 8/1982 |
| EP | 0 035 615 | 12/1986 |
| GB | 1 296 255 | 11/1972 |
| JP | 5-97623 | * 4/1993 |
| WO | WO 82/04259 | 12/1982 |

OTHER PUBLICATIONS

"Tri–Cure Glass Ionomer System," Technical Product Profile, 3M Vitremer™, 3M Brochure, 35 pp. (1992).
"An Outline of Dental Materials and Their Selection," O'Brien and Ryge, Eds., W. B. Saunders Co., Philadelphia, London, Toronto, Title page, 210–211, 216, and 351–353 (1978).
International Search Report.

\* cited by examiner

Primary Examiner—Thurman K. Page
Assistant Examiner—Robert M. Joynes

(57) ABSTRACT

Dental compositions are provided with a fluoride releasing material that is a metal complex described by formula $$M(G)_g(F)_n \text{ or } M(G)_g(ZF_m)_n$$

where
M represents an element capable of forming a cationic species and having a valency of 2 or more,
G is an organic chelating moiety capable of complexing with the element M
Z is hydrogen, boron, nitrogen, phosphorus, sulfur, antimony, arsenic
F is a fluoride atom
g, m and n are at least 1.

27 Claims, No Drawings

USE OF METALLOFLUOROCOMPLEXES FOR DENTAL COMPOSITIONS

FIELD OF THE INVENTION

This invention relates to the use of metallofluorocomplexes in dental compositions.

BACKGROUND

The discovery of the effect of fluoride ion in the prevention and inhibition of caries was a major breakthrough in the preservation of dental health. Subsequent research has demonstrated that the caries resistance was due to the incorporation of fluoride into dental enamel during matrix formation, calcification and pre-eruptive maturation. After the formation and eruption of the tooth crown the surface layers of enamel continue to acquire additional fluoride. This discovery has lead to the development of many dentrifices and dental restorative materials that release fluoride into the surrounding oral environment. Most of these compositions incorporate simple inorganic fluoride salts as the fluoride source. The most common of these is sodium fluoride or sodium fluorophosphate, although compositions containing tin fluorides are becoming increasingly popular.

U.S. Pat. No. 4,629,746 calls for adding simple fluoride salts of rare earth elements (elements 57–71 of the periodic table) into dental compositions, particularly dental restoratives. U.S. Pat. No. 4,515,910 discloses a fluoride releasing interpolymer which is the reaction product of a monomer bearing an anion-exchange site carrying fluoride ions e.g. a quaternary ammonium fluoride. Organic fluoride sources such as those from alkylonium tetrafluoborate sources have been described in U.S. Pat. No. 4,871,786.

A very popular way of releasing fluoride in the oral environment has been the use of glass ionomer cements. In these cases, an ion-leachable fluoride glass is utilized along with an aqueous acidic solution. The decomposition of the glass results in the slow release of fluoride ions. See generally, *Glass Ionomer Cement*. A. D. Wilson and J. W. McLean, Quintessence Publishing Co., Inc. 1988. Many modifications of these cements exist.

SUMMARY OF THE INVENTION

In the present invention, a curable dental composition is provided with a fluoride releasing material that is a metal complex described by formula $$M(G)_g(F)_n \text{ or } M(G)_g(ZF_m)_n$$

where

M represents an element capable of forming a cationic species and having a valency of 2 or more, G is an organic chelating moiety capable of complexing with the element M Z is hydrogen, boron, nitrogen, phosphorus, sulfur, antimony, arsenic is F is a fluoride atom g, m and n are at least 1.

DETAILED DESCRIPTION OF THE INVENTION

This invention provides novel compositions which release fluoride into a surrounding aqueous environment.

Examples of preferred M elements are the metals of groups IIA, IIIA, IVA, and transition and inner transition metal elements of the periodic table. Specific examples include $Ca^{+2}$, $Mg^{+2}$, $Sr^{+2}$, $Zn^{+2}$, $Al^{+3}$, $Zr^{+4}$, $Sn^{+2}$, $Yb^{+3}$, $Y^{+3}$, $Sn^{+4}$. Most preferably, M is $Zn^{+2}$.

The G group, as noted above, is an organic chelating moiety. This chelating moiety may or may not contain a polymerizable group. Although not absolutely essential, in some instances it may be advantageous for the chelating moiety to contain a polymerizable functionality that matches the reactivity of the polymerizable matrix into which it is incorporated:

A wide range of chelating moieties may be used in the present invention. Chelates in which the metal ion is bound in a ring structure of 4–8 members are preferred, with the 5–7 membered ring chelates being particularly preferred. The chelates useful in the present invention are multidentate, and are preferably bi-, tri- or quadra-dentate. Chelates containing hydroxyl or carboxy groups or both are more particularly preferred. Examples of such chelating agents are tartaric acid, citric acid, ethylenediamine tetraacetic acid, salicylic acid, hydroxybenzoic acids, hydroxytartaric acids, nitrilotriacetic acid, salicylic acid, melletic acids, and polyglycols. Chelates containing one or more acid groups derived from phosphorus, boron or sulfur can also be used, with the proviso that the molecular weight of the chelating agent is less than about 1000. Examples of especially suitable metal chelates include complexes of β-diketones and β-ketoesters.

The polymerizable metal-fluoride chelates preferably contain one or more polymerizable groups that match the reactivity of the polymerizable matrix into which it is incorporated. In addition to the chelating functionalities outlined above, these complexes can contain ethylenically unsaturated groups, epoxy groups, ethyleneimine groups and the like.

Preferred G groups include the polyphosphates, such as sodium tripolyphosphate and hexametaphosphoric acid; arninocarboxylic acids, such as ethylenediaminetetraacetic acid, hydroxyethylethylenediaminetriacetic acid, nitrilotriacetic acid, N-dihydroxyethylglycine and ethylenebis (hydroxyphenylglycine); 1,3-diketones, such as acetylacetone, trifluoroacetylacetone and thenoyltrifluoroacetone; hydroxycarboxylic acids, such as tartaric acid, citric acid, gluconic acid, and 5-sulfosalicylic acid; polyamines, such as malic acid, ethylenediamine, triethylenetetramine and triaminotriethylamine; aminoalcohols, such as triethanolamine and N-hydroxyethylethylenediamine; aromatic heterocyclic bases, such as dipyridyl and o-phenanthroline; phenols, such as salicyladehyde, disulfopyrocatechol and chromotropic acid; aminophenols, such as oxime, 8-hydroxyquinoline and oxinesulfonic acid; oximes, such as dimethylglyoxime and salicyladoxime hydroxamic acid and its derivatives; Schiff bases, such as disalicyladehyde 1,2-propylenedimine; tetrapyrroles, such as tetraphenylporphin and phthalocyanine; sulfur compounds, such as toluenedithiol(Dithiol), dimercaptopropanol, thioglycolic acid, potassium ethylxanthate, sodium diethyldithiocarbamate, dithizone, diethyl dithiophosphoric acid and thiourea; synthetic macrocyclic compounds, such as dibenzo[18]crown-6(5), $(CH_3)_6$[14]4,11-dieneN$_4$ (6) and (2.2.2-cryptate) (7); polymeric compounds such as polyethylenimine, polymetharyloylacetone, and poly(p-vinylbenzyliminodiacetic acid); and phosphonic acids, such as nitrilotrimethylenephosphonic acid, ethylenediaminetetra (methylenephosphonic acid) and hydroxyethylidenediphosphonic acid.

Particularly preferred G groups are compounds of the following formulas:

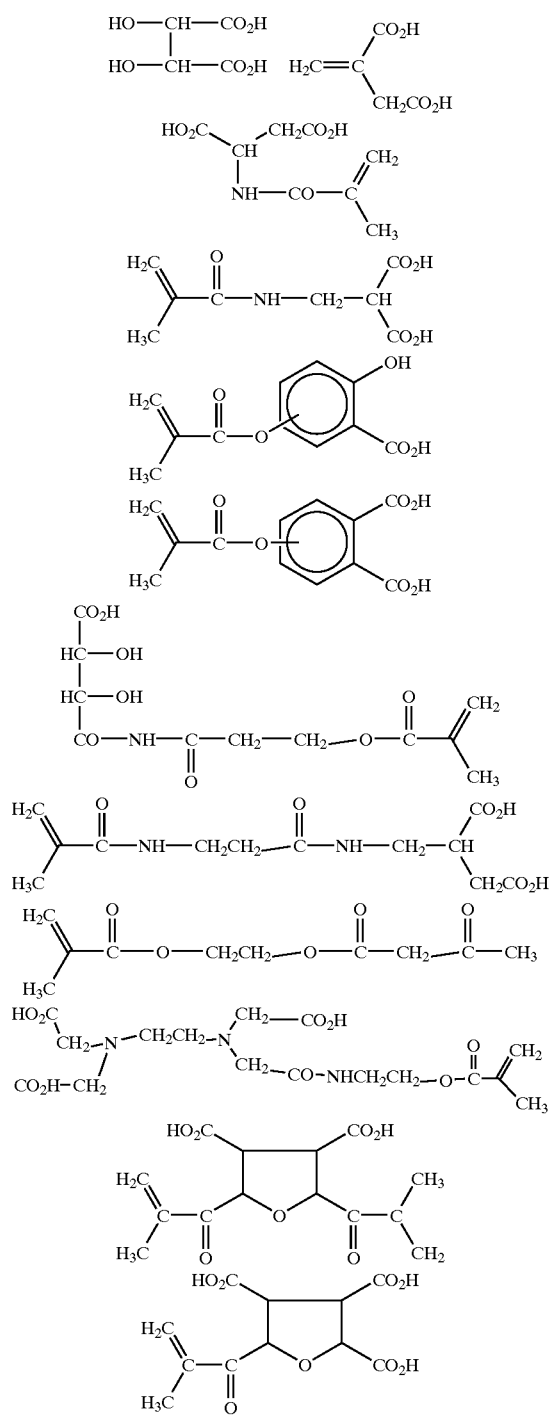

Fluoride is associated with the complexed metal as either a counterion or as a ligand. Thus, the designation (ZF) above indicates that the fluoride is associated with the Z group as a complex, which in turn is associated with the metal as a counterion or as a ligand.

The fluorocomplex materials of the invention can be incorporated into dental compositions that undergo setting reactions by virtue of a complexation reaction other than polymerization. Thus they can form components of zinc phosphate cements, polycarboxylate cements, glass ionomer cements and dental amalgams in order to release or enhance the release of fluoride ions. Additionally, these fluorocomplex materials can be incorporated into compositions that have both a complexation reaction as described above and a polymerization reaction.

Finally, the fluorocomplex materials of the invention can be incorporated into dental compositions that undergo only polymerization reactions as a cure mechanism. Useful polymerizable monomers are described in U.S. Pat. No. 4,871,786. Suitable initiators and fillers can be added to these compositions. In general, the more hydrophilic the resin matrix is the greater the initial fluoride release rate provided all other factors are maintained equal. In some instances, it may be advantageous to increase the water-absorbing property of the polymerizing matrix by incorporating hydrophilic monomers, oligomers, polymers or prepolymers with polymerizing groups. The water absorbing capacity is thereby increased by the incorporation of suitable hydrophilic moieties. Organic moieties suitable for this are pyrrolidone, alkylamides of lower alkyl groups, polyethers, polysulfones, derivatives of sulphonic and carboxylic acids and the like. This type of polymerizable composition is described in more detail below.

The compositions of this invention have utility in dental applications where it is desirable to provide fluoride release into dentition. The specific areas of application include, but are not limited to, sealants, adhesives, bases, temporary and permanent luting cements, orthodontic adhesives and cements, resin-based restoratives, glass ionomer based restoratives, core build-ups, and articles comprised thereof such as crowns, bridges, fillings, orthodontic appliances and removable prosthodontic devices.

Particularly preferred compositions of the present invention comprise at least two sources of fluoride. The first source is the fluoride-containing metal complex as described above. The second source is a fluoride-releasing fluoroaluminosilicate glass. With the use of both materials, excellent fluoride release is provided both in the initial period and over the long term use of the composition.

A particularly preferred dental composition that may contain the metallofluorocomplexes of the present invention is a dental composition comprising a) a polymerizable component, b) a fluoride-releasing material, c) a hydrophilic component, d) a polymerization initiator, and e) an acidic component. This dental composition is substantially free of added water, and has a Water Uptake Value of at least about 1.5 g of water per 100 g composition in 2 weeks.

For purposes of the present invention, the term "substantially free of added water" means that the composition does not contain water that is intentionally added as a non-complexed or coordinated entity. It is understood that many materials, such as metals or glasses, contain water that is taken up from the atmosphere or is present as a coordination complex in its normal state. Water taken up by hygroscopic materials or present as a hydrate is permissibly present in the compositions described herein. Any water that is present in the composition, regardless of source, should not be present in amounts such that the water will have a deleterious effect of the long term properties of the composition. For example, water should not be present in an amount that would facilitate reaction of the fluoride-releasing material with the acidic component so that lumpiness or graininess of the material develops during commercially required storage time.

The polymerizable component of the preferred compositions are compounds, which may be monomers, oligomers, or polymers, containing a polymerizable group. These polymerizable groups may be selected from free radically polymerizable groups, cationically polymerizable groups, or mixtures thereof Preferably, the polymerizable compound has a molecular weight of between about 100 to 5000, and more preferably, has a molecular weight between about 200 and 1000. Mixtures of both higher and lower molecular weight polymerizable materials are also contemplated as providing special benefits in handling properties and ultimate cure material physical properties. In a preferred aspect of the present invention, at least some of the polymerizable material is relatively lower in viscosity than other ingredients of the composition so that it serves a viscosity lowering function in the overall uncured material. Preferably, at least some of the polymerizable material has a viscosity of less than 2000 cp, more preferably less than 500 cp, and most preferably less than 300 cp.

Preferred materials that provide the polymerizable component are the esters of acrylic or methacrylic acid. Examples of these compounds are methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di- acrylate, glycerol mono- and di- methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra- acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl4-cyclohexyl carbamate, di-2-methacryloxyethyl-dimethylcyclohexane dicarbamate, methylene-bis-2-methacryloxyethyl4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl4-cyclohexyl carbamate, di-b 1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acryalte]propane, and the like.

Other preferred polymerizable components can be substituted acryl amides and methacrylamides. Examples are acrylamides, methylene bis-acrylamides, methylene bis-methacrylamide, diacetone/acrylamide diacetone methacylamide, N-alkyl acrylamide and N-alkyl methacrylamide where alkyl is a lower hydrocarbyl unit of 1–6 carbon atoms. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

Alternatively, the polymerizable component may be a cationically cured material, such as epoxy materials, oxetanes, oxolanes, cyclic acetals, lactams, lactones, and vinyl ethers or spirocyclic compounds containing oxygen atoms in the ring.

The cationically polymerizable epoxy resins useful in the compositions of the invention comprise organic compounds having an oxirane ring, i.e.,

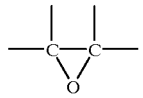

polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, and preferably at least about 1.5 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures containing one, two, or more epoxy groups per molecule. The "average" number of epoxy groups per molecule is determined by dividing the total number of epoxy groups in epoxy-containing material by the total number of epoxy molecules present.

These epoxy-containing materials may vary from low molecular weight monomeric materials to high molecular weight polymers and may vary greatly in the nature of their backbone and substituent groups. For example, the backbone may be of any type and substituent groups thereon can be any group that does not substantially interfere with cationic cure at room temperature. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexene oxide groups such as the epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, incorporated herein by reference.

Further epoxy-containing materials which are particularly useful in the practice of this invention include glycidyl ether monomers of the formula

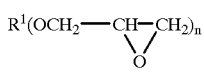

where $R^1$ is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type which can be used in the practice of this invention are described in U.S. Pat. No. 3,018,262, incorporated herein by reference, and in "Handbook of Epoxy Resins" by Lee and Neville, McGraw-Hill Book Co., New York (1967).

There are a host of commercially available epoxy resins which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL4221" or "UVR 6110" or "UVR 6105" from Union Carbide Corp.), 3,4-epoxy-6-methylcyclohexylmethyl-3,4-epoxy-6-methyl-cyclohexene carboxylate (e.g., "ERL4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.), aliphatic epoxy modified with polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN431" and "DEN438" from Dow Chemical Co.), and resorcinol diglycidyl ether (e.g., "Kopoxite" from Koppers Company, Inc.). bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy) cyclohexane-metadioxane (e.g., "ERL4234" from Union Carbide Corp.), vinylcyclohexene monoxide (from Union Carbide Corp.), 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-tert butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1 138" or "GY-281" from Ciba-Geigy Corp.), 9,9-bis[4-(2,3-epoxypropoxy)-phenyl]fluorenone (e.g., "Epon 1079" from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, e.g., epichlorohydrin; alkylene oxides, e.g., propylene oxide, styrene oxide; alkenyl oxides, e.g., butadiene oxide; glycidyl esters, e.g., ethyl glycidate.

The polymers of the epoxy resin may optionally contain other functionalities that do not substantially interfere with cationic cure at room temperature.

Blends of various epoxy-containing materials are particularly contemplated in this invention. Examples of such blends include two or more molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical nature, such as aliphatic and aromatic, or functionality, such as polar and non-polar. Other cationically polymerizable polymers may additionally be incorporated. Particularly preferred epoxy containing composition also contain materials having hydroxyl functionality.

Mixtures of polymerizable materials, including hybrid systems containing both free-radically polymerized components and cationically polymerized components, are also contemplated.

The fluoride-releasing material of the preferred composition may include, in addition to the metallofluoro complexes described above, a naturally occuring or synthetic fluoride minerals, fluoride glass such as fluoroaluminosilicate glass, simple and complex inorganic fluoride salts, simple and complex organic fluoride salts or combinations thereof. Optionally these fluoride sources can be treated with surface treatment agents.

Examples of the fluoride-releasing material are fluoroaluminosilicate glasses described in U.S. Pat. No. 4,3814, 717, which may be optionally treated as described in U.S.

Pat. No. 5,332,429, the disclosures of which are both incorporated by reference herein.

The hydrophilic component can be provided as a monomer, oligomer or polymer. Preferably, it is provided as either a linear homopolymer or copolymer, either of which may optionally be lightly crosslinked. The hydrophilic component is preferably miscible in water at concentrations of about 3% by weight or can absorb at least 2 g of water per hundred g of polymer. Optionally, the hydrophilic component can be a hydrophilic monomer which undergoes polymerization in situ leading to a hydrophilic, water-absorbing polymer.

In many cases, compounds containing acidic functionality are hydrophilic in nature. Such compounds may be useful in the present invention is they satisfy the above hydrophilicity characteristics. It has been found, however, that preferred hydrophilic components for use in the present invention have at least a portion of their hydrophilic properties provided by non-acidic functionalities. Thus, preferred hydrophilic compounds for use in the present invention contain acidic functionality and non-acidic hydrophilic functionality, and most preferred hydrophilic compounds for use in the present invention contain no acidic functionalities.

Examples of hydrophilic components include monomers or polymers such as pyrrolidone, a moiety containing a sulfonate group (SO$_3$), a moiety containing a sulfonic group (SO2), N-oxysuccinimide, N-vinylacetamide and acrylamide.

More specific examples of preferred hydrophilic components are non-ionic polymers or copolymers, e.g. polyalkylene oxides (polyoxymethylene, polyethyleneoxide, polypropylene oxide) polyethers (polyvinylmethyl ether), polyethyleneimine copolymers, polyacrylamides and polymethacrylamides, polyvinylalcohol, saponified polyvinylacetate, polyvinylpyrrolidone, polyvinyloxazolidone, polymers containing N-oxysuccinimdo groups, ionic or ionizable polymers and copolymers containing polyacrylic acid, polymethacrylic acid in unionized, partially neutralized or fully neutralized form, polyethyleneimine and its salts, polyethylene sulfonic acid and polyaryl sulfonic acids in unionized, partially neutralized or fully neutralized form, polyphoshoric and phosphonic acids in unionized, partially neutralized or fully neutralized form.

Generally, any compound having a polar group may provide a hydrophilic aspect to a composition. Preferred hydrophilic compounds may be prepared by reaction of vinylic monomers such as acrylates, methacrylates, crotonates, itaconates and the like that contain polar groups that are acidic, basic or provided as a salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B) and ionic groups (such as quarternary ammonium, carboxylate salt, sulfonic acid salt and the like) and the precursors and protected forms of these groups. More specific examples of such groups follow.

The hydrophilic component may be derived from mono- or multifunctional carboxyl group containing molecules represented by the general formula:

$$CH_2=CR^2G—(COOH)_d$$

where R$^2$=H, methyl, ethyl, cyano, carboxy or carboxymethyl, d=1–5 and G is a bond or a hydrocarbyl radical linking group containing from 1–12 carbon atoms of valence d+1 and optionally substituted with and/or interrupted with a substituted or unsubstituted heteroatom (such as O, S, N and P). Optionally, this unit may be provided in its salt form. The preferred monomers in this class are acrylic acid, methacrylic acid, itaconic acid and N-acryloyl glycine.

The hydrophilic component may, for example, be derived from mono- or multifunctional hydroxy group containing molecules represented by the general formula:

$$CH_2=CR^2—CO—L—R^3—(OH)_d$$

where R$^2$=H, methyl, ethyl, cyano, carboxy or carboxyalkyl, L=O, NH, d=1–5 and R$^3$ is a hydrocarbyl radical of valence d+1 containing from 1–12 carbon atoms. The preferred monomers in this class are hydroxyethyl (meth)acrylate, hydroxypropyl (meth)acrylate, hydroxybutyl (meth)acrylate, glycerol mono(meth)acrylate, tris(hydroxymethyl)ethane monoacrylate, pentaerythritol mono(meth)acrylate, N-hydroxymethyl (meth)acrylamide, hydroxyethyl (meth)acrylamide and hydroxypropyl (meth)acrylamide.

The hydrophilic component may alternatively be derived from mono- or multifunctional amino group containing molecules of the general formula:

$$CH_2=CR^2—CO—L—R^3—(NR^4R^5)_d$$

where R$^2$, L, R$^3$, and d are as defined above and R$^4$ and R$^5$ are H or alkyl groups of 1–12 carbon atoms or together they constitute a carbocyclic or heterocyclic group. Preferred monomers of this class are aminoethyl (meth)acrylate, aminopropyl (meth)acrylate, N,N-dimethylaminoethyl (meth)acrylate, N,N-diethylaminoethyl (meth)acrylate, N,N-dimethylaminopropyl (meth)acrylamide, N-isopropylaminopropyl (meth)acrylamide and 4-methyl-1-acryloyl-piperazine.

The hydrophilic component may also be derived from alkoxy substituted (meth)acrylates or (meth)acrylamides such as methoxyethyl (meth)acrylate, 2(2-ethoxyethoxy)ethyl (meth)acrylate, polyethylene glycol mono(meth)acrylate or polypropylene glycol mono(meth)acrylate.

Hydrophilic components may be derived from substituted or unsubstituted ammonium monomers of the general formula:

$$CH_2=CR^2—CO—L—R^3—(NR^4R^5R^6)_d^{\oplus}Q—$$

where R$^2$, R$^3$, R$^4$, R$^5$, L and d are as defined above, and where R$^6$ is H or alkyl of 1–12 carbon atoms and Q— is an organic or inorganic anion. Preferred examples of such monomers are 2-N,N,N-trimethylammonium ethyl (meth)acrylate, 2-N,N,N-triethylammonium ethyl (meth)acrylate, 3-N,N,N-trimethylammonium propyl (meth)acrylate, N(2-N',N',N'-trimethylammonium) ethyl (meth)acrylamide, N-(dimethyl hydroxyethyl ammonium) propyl (meth)acrylamide etc. where the counterion may be fluoride, chloride, bromide, acetate, propionate, laurate, palmitate, stearate etc. The monomer can also be N,N-dimethyl diallyl ammonium salt of an organic or inorganic counterion.

Ammonium group containing polymers can also be prepared by using as the hydrophilic component any of the amino group containing monomer described above, and acidifying the resultant polymers with organic or inorganic acid to a pH where the pendant amino groups are substantially protonated. Totally substituted ammonium group containing polymers may be prepared by alkylating the above described amino polymers with alkylating groups, the method being commonly known in the art as the Menschutkin reaction.

The hydrophilic component of the invention can also be derived from sulfonic acid group containing monomers, such as vinyl sulfonic acid, styrene sulfonic acid, 2-acrylamido-2-methyl propane sulfonic acid, allyloxybenzene sulfonic acid, and the like. Alternatively, the hydrophilic component may be derived from phosphorous acid or boron acid group-containing monomers. These monomers may be used in the protonated acid form as monomers and the corresponding polymers obtained may be neutralized with an organic or inorganic base to give the salt form of the polymers.

Compositions of the preferred compositions of the present invention contain one or more suitable polymerization initiators, so that the composition may be polymerized in use. The initiator is selected such that it is capable of initiating the polymerization of the polymerizable material. That is, if the polymerizable material is a free radical polymerizable material, the initiator is a free-radical polymerization initiator. Likewise, if the polymerizable material is a cationically polymerizable material, the initiator is a cationic polymerization initiator.

Compositions of the invention that are free-radically polymerized preferably contain one or more suitable photopolymerization initiators that act as a source of free radicals when activated. Such initiators can be used alone or in combination with one or more accelerators and/or sensitizers.

The photoinitiator should be capable of promoting free radical crosslinking of the ethylenically unsaturated moiety on exposure to light of a suitable wavelength and intensity. It also preferably is sufficiently shelf stable and free of undesirable coloration to permit its storage and use under typical dental conditions. Visible light photoinitiators are preferred. The photoinitiator frequently can be used alone, but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.1 to about 5%, based on the total weight of the composition.

The compositions of the present invention may alternatively incorporate a mode of initiation of the polymerization reaction to initiate a crosslinking reaction without the need to expose the system to visible light. A preferred alternative mode for initiation of the polymerization reaction is the incorporation of an oxidizing agent and a reducing agent as a redox catalyst system to enable the dental composition to cure via a redox reaction. Various redox systems is described in U.S. Pat. No. 5,154,762, the disclosure of which is expressly incorporated herein by reference.

The oxidizing agent should react with or otherwise cooperate with the reducing agent to produce free radicals capable of initiating polymerization of the ethylenically unsaturated moiety. The oxidizing agent and the reducing agent preferably are sufficiently shelf stable and free of undesirable coloration to permit their storage and use under typical dental conditions. The oxidizing agent and the reducing agent should also preferably be sufficiently soluble and present in an amount sufficient to permit an adequate free radical reaction rate. This can be evaluated by combining the ethylenically unsaturated moiety, the oxidizing agent and the reducing agent and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include amines (and preferably aromatic amines), ascorbic acid, metal complexed ascorbic acid, cobalt (II) chloride, ferrous chloride, ferrous sulfate, hydrazine, hydroxylamine, oxalic acid, thiourea and salts of a dithionite, thiosulfate, benzene sulfinate, or sulfite anion.

The use of redox initiator systems is generally less preferred to photoinitiator systems, because care must be taken to keep the reducing agent from reacting with the oxidizing agent before polymerization is desired. Generally, the use of a redox system necessitates providing the material in a two-part format. One-part dental compositions utilizing a photoinitiator system are preferred.

For compositions that are polymerized by a cationic mechanism, suitable initiators include salts that are capable of generating cations such as the diaryliodonium, triarylsulfonium and aryldiazonium salts.

The acidic component of the preferred compositions of the present invention is provided by compounds that are monomers, oligomers or polymers of molecular weight less than 10,000 and containing at least one acidic group. The acidic group is preferably selected from oxyacids or thio-oxy acids of B, C, N, S, P. More preferably, the acidic component is a compound that is an acid of C or P. If desired, a precursor to the acid such as an acid anhydride, e.g., 4-Methacryloxyethyl Trimellitate Anhydride (4-META), or ester can be used in place of the acid itself, e.g., to generate the desired acid in situ. Suitable acids include, carboxylic acids, sulfonic acids, and phenols, with carboxylic acids, alkylsulfonic acids, arylsulfonic acids, and phosphonic acids being preferred.

Suitable organic acids include acetic acid, a-chloropropionic acid, 2-acrylamido-2-methylpropane sulfonic acid, acrylic acid, benzenesulfonic acid, benzoic acid, bromoacetic acid, 10-camphorquinone-sulfonic acid, 10-camphorsulfonic acid, chloroacetic acid, citraconic acid, citric acid, dibromoacetic acid, dichloroacetic acid, di-Hema ester of 1,2,4,5 benzenetetracarboxylic acid, 2,4-dinitrophenol, formic acid, fumaric acid, 2-hydroxy4-methoxybenzophenone-5-sulfonic acid, maleic acid, methacrylic acid, 2-naphthalene sulfonic acid, nitric acid, oxalic acid, p-nitrophenol, phenol, phosphoric acid, phosphorous acid esters (such as 2,2'-bis(a-methacryloxy-b-hydroxypropoxyphenyl) propane diphosphonate (Bis-GMA diphosphonate), dibutyl phosphite, di-2-ethyl-hexyl phosphate, di-2-ethyl-hexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), pivalic acid, propionic acid, sulfuric acid, toluene sulfonic acid, tribromoacetic acid, trichloroacetic acid, trifluoroacetic acid, trifluoromethanesulfonic acid, and trihydroxybenzoic acid. Mixtures of such acids can be used if desired. Preferred acids are capable of complexing with a reactive glass.

The mixtures can if necessary also contain other compounds that although they contain acid groups, their salts, or their reactive derivative groups, do not contain polymerizable groups. Preferred in this case are multibasic acids such as tartaric, citric, mellitic, polycarboxylic, polyphosphoric, polyphosphonic, or polysulfonic acids along with chelating agents such as ethylenediamine-tetraacetic acid, and especially their salts.

Particularly preferred compositions of the present invention are those wherein at least a portion of the polymerizable component and at least a portion of the acidic component of the composition are provided by the same chemical compound. Examples of such compounds are monomers, oligomers or polymers of molecular weight less than 10,000 and containing at least one acidic groups and at least one polymerizable group. Preferably, these compounds hav a molecular weight of between about 100–5000, and more preferably between about 200–1000. The acidic group can be oxyacids or thio-oxy acids of B, C, N, S, P. Preferably it is an acid of C or P.

These preferred compounds are defined by the structure
$(P)_p$—$(Q)_q$—$(R)_r$—
where
P=backbone with acidic functionality
Q=backbone with a curable group, e.g. acrylate, methacrylate, epoxy etc
R=backbone of a non-reactive modifying unit
$p \geq 1$, $q > 1$, and r=0 or more.

Especially preferable acid groups are carboxylic acids, sulfonic acids, phoshoric acids, phosphonic acids, and boric acids, the salts of the foregoing acids or precursors of the foregoing acids that are easily converted to these acids in conditions encountered during a dental restorative procedure. Examples of such compounds are acryloyl or methacryloyl substituted polycarboxylic acids, phosphoric acid esters of hydroxyethyl methacrylate, hydroxy propyl methacrylate, acrylates and methacrylates of pentaerythritol dimethacrylate and glyceroldimethacrylate.

Examples of such preferred compounds include the aliphatic carboxy compounds, such as acrylic acid, methacrylic acid, maleic acid, fumaric acid, itaconic acid, crotonic acid, aconitic acid, glutaconic acid, mesaconic acid, tiglicinic acid, 2-chloroacrylic acid, 3-chloroacrylic acid, 2-bromoacrylic acid, 1-methacryloyl malonic acid, 1-acryloyl malic acid, N-methacryloyl and N-acryloyl derivatives of amino acids, and acids such as tartaric acid, citric acid, malic acid that have been further functionalized with an ethylenic functionality. For example, citric acid may be ethylenically functionalized by substituting with an acryloyl or methacryloyl functionality.

Other preferred compounds are the aromatic carboxy compounds, such as benzoic acid, and acryloyl or methacryloyl derivatives of salicyclic acid, trimellitic acid, phthalic acid, and the like.

Reactive fillers suitable for use in the systems of this invention include those that are commonly used with ionomers to form ionomer cements. Examples of suitable reactive fillers include metal oxides such as zinc oxide and magnesium oxide, and ion-leachable glasses, e.g., as described in U.S. Pat. Nos. 3,655,605, 3,814,717, 4,143,018, 4,209,434, 4,360,605 and 4,376,835.

The reactive filler is preferably a finely divided reactive filler. The filler should be sufficiently finely-divided so that it can be conveniently mixed with the other ingredients and used in the mouth. Preferred average particle diameters for the filler are about 0.2 to about 15 micrometers, more preferably about 1 to 10 micrometers, as measured using, for example, a sedimentation analyzer.

Preferred reactive fillers are acid-reactive. Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses. Fillers that are reactive as described above provide excellent handling properties and final composition properties because, when reacted, they impart a gel or partial gel structure to the material.

Most preferred of the reactive fillers are those that release fluoride. Fluoride releasing glasses, in addition to providing good handling and final composition properties as discussed above, provide the benefit of long-term release of fluoride in use, for example in the oral cavity. Fluoroaluminosilicate glasses are particularly preferred. Suitable reactive fillers are also available from a variety of commercial sources familiar to those skilled in the art. For example, suitable fillers can be obtained from a number of commercially available glass ionomer cements, such as "GC Fuji LC" and "Kerr XR" ionomer cement. Mixtures of fillers can be used if desired.

If desired, the reactive filler can be subjected to a surface treatment. Suitable surface treatments include acid washing, treatment with phosphates, treatment with chelating agents such as tartaric acid, treatment with a silane or silanol coupling agent. Particularly preferred reactive fillers are silanol treated fluoroaluminosilicate glass fillers, as described in U.S. Pat. No. 5,332,429 the disclosure of which is expressly incorporated by reference herein.

Non-reactive fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable non-reactive inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable non-reactive organic filler particles include filled or unfilled pulverized polycarbonates, polyepoxides, and the like. Preferred non-reactive filler particles are quartz, submicron silica, and non-vitreous microparticles of the type described in U.S. Pat. No. 4,503,169. Mixtures of these non-reactive fillers are also contemplated, as well as combination fillers made from organic and inorganic materials.

Preferably the surface of the filler particles is treated with a coupling agent in order to enhance the bond between the filler and the polymerizable resin. The use of suitable coupling agents include gamma-methacryloxypropyltrimethoxysilane, gamma-mercaptopropyltriethoxysilane, gamma-aminopropyltrimethoxysilane, and the like.

If desired, the compositions of the invention can contain adjuvants such as cosolvents, pigments, inhibitors, accelerators, viscosity modifiers, surfactants, rheology modifieers, colorants, medicaments and other ingredients that will be apparent to those skilled in the art. Optionally, the compositions may contain stabilizers. The incorporation of stabilizers serves to further improve the color stability of paste:paste compositions. Suitable stabilizers include oxalic acid, sodium metabisulfite, metaphosphoric acid, sodium bisulfite, sodium thiosulfate, and combinations thereof. Oxalic acid and sodium metabisulfite are preferred stabilizers.

Cosolvents useful in the present invention include, but are not limited to, low molecular weight organic solvents. The word "cosolvent", as used herein refers to a material that aids in the dissolution of materials in the composition, in order to form a homogeneous composition. Examples of suitable cosolvents include ethanol, propanol, and glycerol.

The compositions of this invention can be used in a variety of applications in the dental or medical fields in which a material is desired that will adhere well to the surrounding tooth or bone structure. For instance, these compositions can be used as dental restoratives, liners, bases, cements, sealants and as dental or orthodontic adhesives.

The present compositions are preferably provided initially as a one-part paste composition. For purposes of the present invention, a paste is defined as a material wherein the inelastic modules is less than the elastic modulus of the material. Preferably, the paste has a viscosity between about $1\times10^2$ and $1\times10^{11}$ Cps. More preferably, the paste has a viscosity between about $1\times10^7$ and $1\times10^9$ Cps. Viscosity is measured using a rheometer at a shear rate between 0.01 and 0.1 $\sec^{-1}$ at about 25° C. A preferred test protocol is to utilize a Bohlin CS50 controlled stress rheometer (Metric Group, Inc., Bohlin Instruments Division, Cranbury, N.J.) with 20 mm parallel plates and a gap of 2mm. The stress is ramped from 1 Pascal up to a stress sufficient to reach a shear rate of approximately 0.1 $\sec^{-1}$.

Water Uptake Test

Water uptake was measured by forming each composition into disks 20 mm in diameter and 1 mm thick. Both sides of each disk were covered with polyethylene terephthalate ("PET") film and light cured for 30 seconds on each side using two oppositely-disposed 3M™ Visilux™ 2 Visible Light Curing Units with about a 1 cm distance between the output end of the light guide and the sample. The film was then removed and the exposed samples allowed to cure for 1 hour at 37° C./95% relative humidity ("RH"). Each disk was weighed and placed in a glass jar to which was added 25 mL of deionized water. The sample was maintained at 37° C. for a specified time period.

At the specified time, the sample was removed from the jar, the superficial water was removed using a facial tissue or cotton and the sample was immediately weighed. The weight was recorded and the sample was returned to the water in the sample jar. At periodic designated intervals, the above procedure was repeated and the sample weight recorded. At each specified time interval, water uptake for 3 samples of each composition was measured and the average reported in grams per 100 grams of cured composition.

The present invention will be further understood in view of the following examples which are merely illustrative and not meant to limit the scope of the invention. Unless otherwise indicated, all parts and percentages are by weight and all molecular weights are weight average molecular weights.

PREPARATORY EXAMPLE 1

Treated Fluoroaluminosilicate Glass

The ingredients set out below in TABLE 1 were mixed, melted in an arc furnace at about 1350–1450° C., poured from the furnace in a thin stream and quenched using chilled rollers to provide an amorphous single-phase fluoroaluminosilicate glass.

TABLE 1

| Ingredient | Parts |
| --- | --- |
| $SiO_2$ | 37 |
| $AlF_3$ | 23 |
| $SrCO_3$ | 20 |
| $Al_2O_3$ | 10 |
| $Na_3AlF_6$ | 6 |
| $P_2O_5$ | 4 |

The glass was ball-milled to provide a pulverized frit with a surface area of 2.5–3.2 $m^2/g$ measured using the Brunauer, Emmet and Teller (BET) method.

A silanol solution was prepared by mixing together 2.4 parts gamma-methacryloxypropyl trimethoxysilane ("A-174", Union Carbide Corp.), 12.6 parts methanol, 36.5 parts water and 0.33 parts acetic acid. The mixture was stirred magnetically for 60 minutes at ambient temperature, added to 60.8 parts of the glass powder and slurried for 30 minutes at ambient temperature. The slurry was poured into a plastic-lined tray and dried for 10 hours at 80° C. The silanol treated dried powder was sieved through a 60 micrometer mesh screen.

PREPARATORY EXAMPLE 2

Treated OX-50

A-174 (3.7g) was added with stirring to 50 g of deionized water acidified to pH 3–3.3 by dropwise addition of trifluoroacetic acid. The resultant mixture was stirred at about 25° C. for 1 hour at which time 95 g of OX-50 were added to the mixture with continued stirring for 4 hours. The slurry was poured into a plastic-lined tray and dried at 35° C. for 36 hours. The silanol treated dried powder was sieved through a 74 micrometer mesh screen.

PREPARATORY EXAMPLE 3

Treated Zirconia: Silica Filler 25.5 Parts silica sol ("LUDOX" LS, E.I. duPont de Nemours & Co.) were acidified by the rapid addition of 0.255 parts concentrated nitric acid. In a separate vessel, 12.9 parts ion-exchanged zirconyl acetate (Magnesium Elecktron Inc.) were diluted with 20 parts deionized water and the resultant solution acidified with 0.255 parts concentrated nitric acid. The silica sol was pumped into the stirred zirconyl acetate solution and mixed for one hour while filtering the stirred mixture through "CUNO" 5 micrometer and 1 micrometer filters (Commercial Intertech Corp.). The stirred, filtered mixture was further filtered though a 1 micrometer "HYTREX" filter (Osmonics, Inc.) followed by a 0.22 micrometer "BALSTRON" filter (Balston Inc.). The filtrate was poured into trays to a depth of about 25 mm and dried at 65° C. in a forced air oven for about 24 hours. The resultant dried material was removed from the oven and tumbled through a rotary tube furnace (Harper Furnace Corporation) preheated to 600° C. to provide 21 parts of calcined microparticles. The calcined microparticles were comminuted in a tumbling ball mill until all of the microparticles were less than 10 micrometers in particle diameter. 0.3 Part portions of the milled microparticles were placed in ceramic saggers and fired in an electric kiln (Harper Furnace Corporation) in air at 825° C. for 1 hour. The fired microparticles were allowed to cool in air. The cooled microparticles were slurried in hydrolyzed A-174 silane at a ratio of 11.1 parts silane to 100 parts microparticles, dried in a forced air oven and screened through a 74 micrometer mesh screen.

EXAMPLE 1

Preparation of Polymerizable Component "A1"

Citric acid (400g) was dissolved in 2 L of tetrahydrofuran ("THF") in a reaction vessel fitted with a mechanical stirrer, condenser, addition funnel and air inlet tube. To the resultant homogenous solution was added 0.52 g butylated hydroxytoluene ("BHT"), 0.5 g of triphenylantimony ("TPS") and 0.98 g dibutyltin dilaurate ("DBTDL"). Dry air was introduced into the reaction mixture through the inlet tube. 2-Isocyanatoethyl methacrylate ("IEM"; 161.5 g; 1.04 moles) was added dropwise through the addition funnel so as to maintain the reaction temperature at about 40° C. The reaction was followed by infrared spectroscopy ("IR"). After all the IEM had been added and the IR spectrum no longer showed the presence of isocyanate group, the solvent was removed under vacuum from the reaction mixture and the resultant viscous liquid was dried. Nuclear magnetic resonance spectroscopy ("NMR") confirmed the presence of added methacrylate functionalities and the retention of carboxy groups.

EXAMPLE 2

Preparation of Polymerizable Component "A2"

Polyacrylic acid (8.64 g; molecular weight 2,000) and 75 mL THF were added to a reaction flask equipped with a stirrer, condenser, addition funnel and air inlet tube. After stirring at a bath temperature of 50–70° C. for 2–3 hours, a cloudy solution was obtained. The temperature of the bath was maintained at 40–50° C. and a solution containing 0.093 g BHT, 0.093 g TPS and 0.64 g DBTDL in 5 mL of dry THF was added to the reaction mixture. IEM (9.3 g) was added dropwise through the addition funnel over a period of 1 hour. The mixture was allowed to stir until the IR spectrum showed complete disappearance of the isocyanate band at which time the reaction mixture was poured into petroleum ether. A white, solid polymer precipitated and was isolated by filtration, washed and dried under vacuum.

EXAMPLE 3

Preparation of Metal Fluorocomplexes

Performed metal fluorocomplexes DI-DXI were independently prepared by dissolving the quantity of the carboxylic acid complexing agent set out in TABLE 2 in water. For Complex nos. DI-DIX, zinc fluoride powder was slurried with each aqueous solution for about one-half hour, after which time the slurry was poured into a shallow tray and dried at 55° C. overnight. Each complex was then sieved through a 100 micrometer mesh screen to provide a free-flowing powder.

Complex nos. DX and DXI were prepared as detailed for the zinc complexes except that 20 g aluminum trifluoride and 20 g zirconium tetrafluoride respectively were substituted for the zinc fluoride and the resultant complexes were sieved through a 74 micrometer mesh screen. Complex no. DXII was prepared by mixing the zinc fluoride with a mixture of acetoacetoxyethylmethacrylate ("AAEM"; Eastman Chemicals, Tenn.), 10 g ethanol and 5 g deionized water. The resultant mixture was allowed to stir for 12 hours at ambient temperature. The solid was then collected by filtration and dried under vacuum at 45° C. for 12 hours. The dried solid was crushed with a mortar and pestle to yield a fine powder of Complex no. DXII.

TABLE 2

| Complex No. | Complexing Agent | | Water (g) | $ZnF_2$ (g) |
| --- | --- | --- | --- | --- |
| | Type | Amount (g) | | |
| DI | Tartaric acid | 20 | 20 | 20 |
| DII | Tartaric acid | 20 | 20 | 80 |
| DIII | Tartaric acid | 30 | 20 | 20 |
| DIV | Tartaric acid | 20 | 20 | 30 |
| DV | N-methacryloyl glutamic acid | 20 | 20 | 20 |
| DVI | Itaconic acid | 20 | 300 | 80 |
| DVII | Itaconic acid | 20 | 300 | 40 |
| DVIII | Itaconic acid | 25 | 350 | 25 |
| DIX | Itaconic acid | 30 | 380 | 20 |
| DX | Tartaric acid | 20 | 20 | — |
| DXI | Tartaric acid | 20 | 20 | — |
| DXII | AAEM | 20 | — | 10 |

EXAMPLE 4

Preparation of Hydrophilic Component "C1"

A glass reaction flask equipped with magnetic stirrer, two addition funnels connected to peristaltic pumps, thermometer, gas inlet tube and reflux condenser was charged with 300 mL of dry THF. One addition funnel was charged with a solution of ethylmethacrylate (18.24 g; 0.16 moles), acrylic acid (28.8 g; 0.4 moles), N-vinylpyrrolidone ("NVP"; 26.98 g; 0.24 moles) and THF to a volume of 200 mL. The second addition funnel was charged with a solution of 0.82 g azobisisobutyronitrile ("AIBN") in 60 mL THF. Both solutions were purged with dry nitrogen for 15 minutes. The reaction vessel was heated to 60° C. and the charges from both addition funnels were added via the peristaltic pumps over a course of 6 hours. After addition was complete, the reaction was stirred at 60° C. overnight. Then 300 mL of dry dimethylformamide ("DMF") was added to the reaction vessel and the temperature lowered to 40° C. BHT (0.094 g), TPS (0.094 g) and DBTDL (0.644 g) were added to the reaction mixture and the nitrogen in the inlet tube was switched to dry air. A solution of IEM (18.6 g; 0.12 mole) in 45 mL THF was added dropwise to the reaction mixture over 2 hours. The reaction mixture was then allowed to stir at 40° C. for an additional hour. The solvents were partially removed under vacuum to reduce the volume to about one-half of the original and the resultant solution poured into ethyl acetate. The precipitated polymer was collected by filtration, washed and dried under vacuum.

EXAMPLE 5

Preparation of Hydrophilic Component "C2"

A glass reaction flask equipped with magnetic stirrer, two addition funnels connected to peristaltic pumps, thermometer, gas inlet tube and reflux condenser was charged with 500 mL of dry THF. One addition funnel was charged with a solution of ethylmethacrylate (34.25 g; 0.3 moles), acrylic acid (50.4 g; 0.7 moles) and THF to a volume of 200 mL. The second addition funnel was charged with a solution of 0.82 g AIBN in 60 mL THF. The solutions were purged with dry nitrogen for 15 minutes. The reaction vessel was heated to 60° C. and the charges from both addition funnels were added via the peristaltic pumps over a course of 6 hours. After addition was complete, the reaction was stirred at 60° C. overnight. Then the reaction temperature was lowered to 35° C. BHT (0. 165 g), TPS (0.165 g) and DBTDL (1.13 g) were added to the reaction mixture and the nitrogen in the inlet tube was switched to dry air. A solution of IEM (32.55 g; 0.21 moles) in 200 mL THF was added dropwise to the reaction mixture over 2 hours. The reaction mixture was then allowed to stir at 35–40° C. for an additional hour. The solvents were partially removed under vacuum to reduce the volume to about one-third of the original and the resultant solution poured into ethyl acetate. The precipitated polymer was collected by filtration, washed and dried in under vacuum.

EXAMPLE 6

Preparation of Hydrophilic Component "C3"

A glass reaction flask equipped with magnetic stirrer, two addition funnels connected to peristaltic pumps, thermometer, gas inlet tube and reflux condenser was charged with 500 mL of dry THF. One addition funnel was charged with a solution of ethylmethacrylate (17.12 g; 0.15 moles), acrylic acid (50.4 g; 0.7 moles), methacrylic acid (12.9 g; 0.15 moles) and THF to a volume of 200 mL. The second addition funnel was charged with a solution of 0.82 g of AIBN in 60 mL THF. Both solutions were purged with dry nitrogen for 15 minutes. The reaction vessel was heated to 60° C. and the charges from the addition funnels were added via the peristaltic pumps over a course of 6 hours. After the addition was complete, the reaction was stirred at 60° C. overnight. Then the reaction temperature was lowered to 35° C. BHT (0.165 g), TPS (0.165 g) and DBTDL (1.13 g) were added to the reaction mixture. The nitrogen in the inlet tube was switched to dry air. A solution of IEM (32.55 g; 0.21 mole) in 200 mL THF was added dropwise to the reaction mixture over 2 hours. The mixture was then allowed to stir at 35–40° C. for an additional hour. The solvents were partially removed under vacuum to reduce the volume to about one-third of the original and the resultant solution poured into ethyl acetate. The precipitated polymer was collected by filtration, washed and dried under vacuum.

EXAMPLE 7

Preparation of Hydrophilic Component "C4"

A glass reaction flask equipped with magnetic stirrer, two addition funnels connected to peristaltic pumps, thermometer, gas inlet tube and reflux condenser was charged with 210 mL of dry THF. One addition funnel was charged with a solution of acrylic acid (50.4 g; 0.7 moles), NVP (33.3 g; 0.3 moles) and THF to a volume of 250 mL. The second addition funnel was charged with a solution of 0.82 g AIBN in 60 mL THF. Both solutions were purged with dry nitrogen for 15 minutes. The reaction vessel was heated to 60° C. and the charges from both addition funnels were added via the peristaltic pumps over a course of 4 hours. After addition was complete, 22 mL of dry DMF was added and the reaction was stirred at 60° C. overnight. The reaction temperature was then lowered to 35° C. BHT (0.15 g), TPS (0.15 g) and DBTDL (1.03 g) were added to the reaction mixture and the nitrogen in the inlet tube was switched to dry air. A solution of IEM (32.55 g; 0.21 mole) in 200 mL THF was added dropwise to the reaction mixture over 2 hours. The reaction mixture was then allowed to stir at 35–40° C. for an additional 24 hours. The solvents were partially removed under vacuum to reduce the volume to about one-third of the original and the resultant solution poured into ethyl acetate. The precipitated polymer was collected by filtration, washed and dried under vacuum.

EXAMPLE 8

Pastes were prepared by mixing the ingredients shown in TABLE 3. The specified quantities of polymerizable component A1 of EXAMPLE 1, glycerol dimethacrylate ("GDMA"; Rohm Tech, Inc., Malden, Mass.) and 1.1 g or no poly(N-vinyl pyrrolidone) ("PVP"; International Specialty Products, Wayne, N.J.) were thoroughly mixed with 0.095 g camphorquinone ("CPQ") and 0.37 g ethyl(4-dimethylamino)benzoate ("EDMAB"). A portion of the resultant mixture was combined with the specified amounts of the glass of PREPARATORY EXAMPLE 1 ("PE1")+2% OX-50 of PREPARATORY EXAMPLE 2 ("PE2") and 4 g or no Complex DI from TABLE 2. The pastes were either hand-mixed or mechanically mixed using a double planetary mixer.

TABLE 3

| Run No. | Component A1 of Ex. 1 (g) | GDMA (g) | PVP (g) | Glass of PE1 + 2% OX-50 of PE2 (g) | Complex DI of Ex. 3 (g) |
| --- | --- | --- | --- | --- | --- |
| 1 | 7.0 | 13.9 | 1.1 | 74.0 | 4 |
| 2 | 7.0 | 13.9 | 1.1 | 78.0 | 0 |
| 3 | 7.3 | 14.7 | 0 | 74.0 | 4 |
| 4 | 7.3 | 14.7 | 0 | 78.0 | 0 |

Water uptake of each composition in TABLE 3 as well as that of Dyract™ Light Cured Compomer ("Dyract"; Dentsply International Inc.) was measured on day 7 and day 14 using the procedure described in the Water Uptake Test. The results are set out in TABLE 4.

Incremental fluoride release of each composition was measured after 3 days and compared with that of Dyract. Disks of each composition were prepared and cured as described for the Water Uptake Test. Each disk was placed in a jar containing 25 mL of deionized water at 37° C.

A fluoride-selective electrode, Orion Model 96-09-00 (from Orion Research Inc., Cambridge, Mass.) was used to quantify the amount of fluoride ion released from the sample in the water. The electrode was calibrated using Fluoride Activity Standards #940907 and #040908, a 100 parts per million ("ppm") and a 10 ppm respectively, fluoride standard fluid (both from Orion Research Inc.).

For the measurement of fluoride ions released into the water, 10 mL of the sample solution was transferred on the day specified to a 60 mL beaker and 10 mL of TISAB solution (total ionic strength adjustment buffer; Orion Research Inc., Cambridge, Mass.) was added to the beaker. The contents were mixed for 10 seconds. The calibrated fluoride-selective electrode was placed in the solution and the ppm $F^-$ were recorded and converted to micrograms of $F^-$ per $cm^2$ of the cured disk. The residual liquid was then removed from the sample jar and replaced with a fresh 25 mL quantity of deionized water. The sample jar was transferred to a 37° C. oven for the specified interval in days, at which time, the sample jar was removed from the oven and the ppm $F^-$ released during that interval were measured as described above. Micrograms of $F^-$ per $cm^2$ of the cured disk were again calculated and these values were reported as a function of time of storage in the water. Fluoride release values for 3 samples of each composition were measured and the average recorded. The results are set out in TABLE 4.

TABLE 4

| Run No. | Water Uptake in g/100 g of Cured Composition Measured on Day | | $\mu g/cm^2$ $F^-$ Released |
|---|---|---|---|
| | 7 | 14 | After 3 Days |
| 1 | 1.7 | 1.9 | 43.38 |
| 2 | 1.9 | 2.1 | 26.03 |
| 3 | 1.5 | 1.8 | 34.70 |

TABLE 4-continued

| Run No. | Water Uptake in g/100 g of Cured Composition Measured on Day | | $\mu g/cm^2$ $F^-$ Released |
|---|---|---|---|
| | 7 | 14 | After 3 Days |
| 4 | 1.6 | 1.9 | 19.52 |
| Dyract | 1.1 | 1.2 | 2.2 |

The incremental fluoride release data in TABLE 4 show that although Run nos. 1–4 with a fluoroaluminosilicate glass in a hydrophilic resin matrix showed good fluoride release compared to a commercial one-paste fluoride releasing material, Dyract, the addition of a metallo-fluorocomplex to the compositions of Run nos. 1 and 3 substantially increased the fluoride release.

EXAMPLE 9

Pastes were prepared by mixing the ingredients shown in TABLE 5. The specified quantities of polymerizable component A1 of EXAMPLE 1, GDMA and component C were thoroughly mixed with CPQ at a concentration of 0.42 parts per hundred and EDMAB at a concentration of 1.65 parts per hundred. A portion of the resultant mixture was combined with the specified amounts of the glass of PE1+2% OX-50 of PE2 and the Complex of EXAMPLE 3 as outlined in TABLE 5. The pastes were either hand-mixed or mechanically mixed using a double planetary mixer.

For determination of compressive strength ("CS") and diametral tensile strength ("DTS"), the composition of each run no. was packed into a 4 mm inside diameter glass tube, capped with silicone rubber plugs and axially compressed at about 0.28 MPa for 15 minutes, then light cured for 80 seconds by exposure to two oppositely-disposed Visilux units. Each sample was then irradiated for 30 seconds using a Dentacolor XS unit (Kulzer). Cured samples were cut on a diamond saw to form cylindrical plugs 8 mm long for measurement of CS and 2 mm long for measurement of DTS. The plugs were stored in distilled water at 37° C. for 24 hours. CS and DTS values for each composition were measured according to ADA ("American Dental Association") specification No. 9 and ADA specification No. 27 respectively.

TABLE 5

| Run No. | Component A1 Ex. 1 (g) | GDMA (g) | Component C | | Glass of PE1 + 2% OX-50 of PE2 (g) | Complex of Ex. 3 | | CS (MPa) | DTS (MPa) |
|---|---|---|---|---|---|---|---|---|---|
| | | | Ex. | Amount (g) | | No. | Amount (g) | | |
| 1 | 7.15 | 14.30 | 4 | 0.55 | 76 | DI | 2 | 346 | 44.8 |
| 2 | — | 21.45 | 4 | 0.55 | 76 | DI | 2 | 320 | 41.6 |
| 3 | 7.00 | 13.90 | 5 | 1.1 | 76 | DI | 2 | 367 | 54.8 |
| 4 | 7.15 | 14.30 | 5 | 0.55 | 76 | DI | 2 | 376 | 50.1 |
| 5 | 7.15 | 14.30 | 6 | 0.55 | 76 | DI | 2 | 378 | 55.5 |
| 6 | 7.00 | 13.90 | 6 | 1.10 | 76 | DV | 2 | 288 | 37.6 |
| 7 | 7.00 | 13.90 | PVP* | 1.10 | 76 | DI | 2 | 368 | 57.7 |
| 8 | 7.00 | 13.90 | PVP | 1.10 | 74 | DI | 4 | 341 | 42.2 |
| 9 | 7.00 | 13.90 | PVP | 1.10 | 72 | DI | 6 | 348 | 43.6 |
| 10 | 7.00 | 13.90 | PVP | 1.10 | 76 | DV | 2 | 338 | 47.6 |
| 11 | 7.00 | 13.90 | PVP | 1.10 | 72 | DV | 6 | 336 | 34.5 |
| 12 | 7.00 | 13.90 | PVP | 1.10 | 72 | DI | 6 | 341 | 52.3 |
| 13 | 7.00 | 13.90 | 5 | 1.10 | 76 | DI | 2 | 373 | 50.2 |
| 14 | 7.00 | 14.0 | 7 | 0.52 | 78 | DI | 4 | 290 | 48.3 |

*Poly(N-vinyl pyrrolidone); International Specialty Products, Wayne, NJ.

The CS and DTS of the paste compositions of Run nos. 1–14 were superior to the mechanical properties of two commercial fluoride releasing materials, 3M™ Vitremer™ Glass Ionomer Core Build-up Restorative ("Vitremer"; 3M) with a CS of 214 MPa and Dyract with a CS of 262 MPa.

Water uptake of the compositions of Run nos. 3, 5 and 7 in TABLE 5 as well as that of Dyract was measured on days 5, 12 and 28 using the procedure described in the Water Uptake Test. The results are set out in TABLE 6.

Incremental fluoride release of the compositions of Run nos. 1, 3, 7, 10 and 11 as well as that of Dyract and Vitremer was measured on days 4, 8, 14, 21 and 27 using the procedure described in EXAMPLE 8. The results are set out in TABLE 6.

TABLE 6

| Run No. | Water Uptake in g/100 g of Cured Composition Measured on Day | | | Incremental F⁻ Release in $\mu g/cm^2$ Measured on Day | | | | |
|---|---|---|---|---|---|---|---|---|
| | 5 | 12 | 28 | 4 | 8 | 14 | 21 | 27 |
| 1 | — | — | — | 28.3 | 17.6 | 36.4 | 25.3 | 20.8 |
| 3 | 1.6 | 2.03 | 2.47 | 17.1 | 14.2 | 20.5 | 20.8 | 19.3 |
| 5 | 1.69 | 2.09 | 2.56 | — | — | — | — | — |
| 7 | 1.6 | 2.17 | 2.54 | 19.1 | 16.5 | 23.4 | 18.7 | 19.5 |
| 10 | — | — | — | 18.2 | 15.3 | 21.2 | 22.8 | 20.4 |
| 11 | — | — | — | 52.1 | 31.8 | 48.1 | 49.1 | 35.6 |
| Dyract | 0.65 | 1.05 | 1.26 | 8.1 | 10.7 | 13.4 | 13.1 | 16.9 |
| Vitremer | — | — | — | 33.3 | 17.6 | 36.4 | 27.5 | 22.1 |

The data in TABLE 6 show that compositions containing the fluorocomplex salts exhibited fluoride release that was much higher than that of a commercial fluoride-releasing one-paste material, Dyract, and was comparable to that of a water-based powder:liquid glass ionomer material, Vitremer.

EXAMPLE 10

Three resin mixtures were prepared by mixing together 7.0 g polymerizable component A1 of EXAMPLE 1, 13.9 g GDMA, 1.1 g PVP, 0.095 g CPQ and 0.37 g EDMAB to provide a homogeneous mixture. Pastes were then compounded by adding to each mixture 74 g of a blend of the glass of PE1, 2% OX-50 of PE2 and 4.0 g of the designated Complex from TABLE 2. All three resultant pastes were stable at room temperature whereas control pastes prepared using untreated zinc fluoride showed substantial thickening on standing and became crumbly after 24 hours.

Using the procedure described in EXAMPLE 8, incremental fluoride release of the compositions of Run nos. 1–3 was measured and compared with that of Dyract and Vitremer. The results are set out in TABLE 7.

The incremental fluoride release results in TABLE 7 show that paste compositions of the invention containing fluorocomplex salts showed much higher fluoride release compared to a commercial one-paste fluoride-releasing material, Dyract. The amount of fluoride released was comparable to a water-based powder:liquid glass ionomer, Vitremer.

EXAMPLE 11

Two resin mixtures were prepared by mixing 11.0 g Bis-GMA, 11.0 g TEGDMA, 0.06 g CPQ and 0.12 g EDMAB to provide a homogeneous mixture. Pastes were then compounded by adding to each mixture the amount of a blend of the glass of PE1, 2% OX-50 of PE2 and 4.0 g or no Complex DI from TABLE 2 as set out in TABLE 8.

Incremental fluoride release of each composition was measured after 3 days using the procedure described in EXAMPLE 8. The results are set out below in TABLE 8.

TABLE 8

| Run No. | Glass of PE1 + 2% OX-50 of PE2 (g) | Complex DI of Ex. 3 (g) | $\mu g/cm^2$ F⁻ Released After 3 Days |
|---|---|---|---|
| 1 | 74.0 | 4.0 | 4.55 |
| 2 | 78.0 | 0 | 0.11 |
| Dyract | — | — | 2.2 |

The data in TABLE 8 show that although the use of the Bis-GMA/TEGDMA resin system of TABLE 8 decreases the overall fluoride release compared to the more hydrophilic matrix used for EXAMPLE 8, the amount of fluoride ion released was still higher for Run no. 1 than that of Run no. 2 which did not contain the zincfluorocomplex and was comparable to a commercial fluoride-releasing one-paste material, Dyract.

TABLE 7

| Run No. | Complex from Table 2 | Incremental F⁻ Released in $\mu g/cm^2$ Measured on Day | | | | | | | | |
|---|---|---|---|---|---|---|---|---|---|---|
| | | 1 | 2 | 3 | 4 | 5 | 6 | 7 | 14 | 21 |
| 1 | DII | 79.53 | 28.20 | 32.53 | 18.08 | 17.35 | 14.46 | 8.68 | 35.43 | 20.24 |
| 2 | DI | 79.53 | 20.24 | 21.69 | 13.01 | 9.40 | 10.12 | 7.23 | 27.83 | 17.21 |
| 3 | DVII | 79.53 | 36.15 | 26.75 | 20.24 | 16.63 | 15.91 | 10.85 | 44.54 | 22.27 |
| Dyract | — | 7.95 | 1.95 | 2.02 | 1.37 | 2.46 | 1.45 | 1.45 | 4.55 | 3.54 |
| Vitremer | — | 65.07 | 16.63 | 13.01 | 10.12 | 8.68 | 6.51 | 5.06 | 27.83 | 16.70 |

EXAMPLE 12

Four resin mixtures were prepared by mixing 7.35 g polymerizable component A1 of EXAMPLE 1, 14.65 g GDMA, 0.095 g CPQ and 0.37 g EDMAB to provide a homogeneous mixture. Pastes were then compounded by adding to each mixture the filler type and amount and 2.0 g or none of Complex D1 from TABLE 2 as set out in TABLE 9.

Cumulative fluoride release was measured on disks of the compositions prepared and cured as described for the Water Uptake Test. Each disk was placed in ajar of phosphate buffer prepared by mixing 0.7 g $KH_2PO_4$ and 0.71 g $Na_2HPO_4$ in 1 liter of deionized water to provide a 0.01M solution having a pH of 6.8–7.0 at 37° C.

A calibrated fluoride-selective electrode as described for incremental fluoride release in EXAMPLE 8 was placed in the buffer solution containing the disk on the days designated in TABLE 9 and ppm $F^-$ recorded. Micrograms of $F^-$ per $cm^2$ of the cured disk were then calculated and these values were reported as a function of time of storage in the buffer. Fluoride release values for 3 samples of each composition were measured and the average reported in TABLE 9. The composition of Run no. 4 showed no measurable fluoride release.

TABLE 9

| Run No. | Type | Filler | Amount (g) | Complex DI Ex. 3 (g) | Cumulative $F^-$ Release in $\mu g/cm^2$ Measured on Day 0 | 7 | 24 |
|---|---|---|---|---|---|---|---|
| 1 | Glass of PE1 + 2% OX-50 of PE2 | | 78 | 0 | 1 | 30 | 45 |
| 2 | Glass of PE1 + 2% OX-50 of PE2 | | 76 | 2 | 2 | 45 | 95 |
| 3 | PREPARATORY EXAMPLE 3 | | 76 | 2 | 1 | 20 | 35 |
| 4 | PREPARATORY EXAMPLE 3 | | 78 | 0 | — | — | — |

The data in TABLE 9 show that the incorporation of a fluorocomplex increased the fluoride release of the compositions of Run nos. 2 and 3. This effect was exhibited even when no other acid-reactive filler was incorporated into the system. Thus both Run nos. 3 and 4 contained a non-acid reactive filler, but only Run no. 3, which contained a fluorocomplex salt, showed appreciable fluoride release.

EXAMPLE 13

A stock liquid was made up by blending 219 g polymerizable component A1 of EXAMPLE 1, 400 g GDMA, 30 g PVP, 11 g EDMAB and 2.8 g CPQ. Six pastes were then formulated using 12.6 g of the stock liquid, 43.8 g of the glass of PE1, 1.2 g of OX-50 of PE2 and 2.4 g of the Complex of EXAMPLE 3 identified in TABLE 10. The CS and DTS of the compositions were measured according to the procedure detailed in EXAMPLE 9.

TABLE 10

| Run. No. | Complex of Ex. 3 | CS (MPa) | DTS (MPa) |
|---|---|---|---|
| 1 | DI | 324 | 53.8 |
| 2 | DIII | 324 | 51.7 |
| 3 | DIV | 331 | 51.0 |
| 4 | DVII | 310 | 53.1 |
| 5 | DVIII | 303 | 48.3 |
| 6 | DIX | 317 | 55.2 |

The data in TABLE 10 show that one-paste compositions containing a hydrophilic resin matrix and zincfluorocomplexes provided cured specimens exhibiting excellent mechanical properties.

EXAMPLE 14

Two pastes were formulated using 12.4 g of the stock liquid of EXAMPLE 13, 43.8 g of the glass of PE1, 1.2 g of OX-50 of PE2 and 2.4 g of the aluminumfluorocomplex or the zirconiumfluorocomplex of EXAMPLE 3. A third paste was formulated as described for the first two pastes, except that 12.6 g of the stock liquid of EXAMPLE 13 was used and the fluorocomplex was DXII. CS and DTS was measured according to the procedure described in EXAMPLE 9 and incremental fluoride release was measured according to the procedure detailed in EXAMPLE 8.

TABLE 11

| Run No. | Complex of Ex. 3 | CS (MPa) | DTS (MPa) | Incremental $F^-$ Release in $\mu g/cm^2$ Measured on Day 1 | 7 |
|---|---|---|---|---|---|
| 1 | DX | 304 | 52.2 | 24.5 | 4.8 |
| 2 | DXI | 312 | 51.7 | 44.8 | 14.2 |
| 3 | DXII | 345 | 50.3 | 88.9 | 13.1 |

The data in TABLE 11 show additional examples of pastes containing metallo-fluorocomplexes of various metals and ligands. These pastes exhibited excellent mechanical properites as well as very high fluoride release.

EXAMPLE 15

A stock solution was prepared by dissolving 40 g GDMA, 3 g PVP, 1.1 g benzoyl peroxide and 0.088 g BHT. Then 8.4 g of the stock solution was combined with 4.2 g of the polymerizable component A1 of EXAMPLE 1. The resulting homogeneous liquid was combined with 43.8 g of the glass of PE1, 1.2 g OX-50 of PE2 and 2.4 g of Complex DI of EXAMPLE 3 to provide a Paste "A".

Three Paste "B" formulations were prepared by combining 43.8 g of the glass of PE1, 1.2 g OX-50 of PE2 and 2.4 g of Complex DI of EXAMPLE 3 with 12.6 g of the ingredients set out below in TABLE 12.

TABLE 12

| Paste B Liquid Ingredients | Paste B1 (g) | Paste B2 (g) | Paste B3 (g) |
|---|---|---|---|
| CD-541[1] | 47.5 | — | — |
| $PEG_{600}DMA$[2] | — | 23.7 | — |
| UDMA[3] | — | 23.7 | 35 |
| PVP | 2.5 | 2.5 | 2.5 |
| HEMA[4] | 10 | 10 | 12.5 |
| DMAPE[5] | 1.5 | 1.5 | 1.5 |

[1]Sartomer, Exton, PA.
[2]Polyethyleneglycol-600 dimethacrylate (Sartomer).
[3]Urethane dimethacrylate (Rohm Tech, Inc., Malden, MA).

TABLE 12-continued

| Paste B Liquid Ingredients | Paste B1 (g) | Paste B2 (g) | Paste B3 (g) |
|---|---|---|---|

[4] 2-Hydroxyethyl methacrylate.
[5] 4-(Dimethylamino)phenethanol.

Compositions were prepared by combining four parts of Paste A with one part of Paste B1, B2 and B3 respectively. Set time was measured according to ISO specification 9917 and CS and DTS were measured according to the procedure described in EXAMPLE 9.

TABLE 13

| Run. No. | Paste B | Set Time (min.:sec.) | CS (MPa) | DTS (MPa) |
|---|---|---|---|---|
| 1 | B1 | 4:00 | 310 | 44.8 |
| 2 | B2 | 3:30 | 303 | 37.9 |
| 3 | B3 | 2:30 | 255 | 27.6 |

The data in TABLE 13 illustrate two-paste compositions containing a hydrophilic resin matrix and a fluorocomplex that cured upon mixing to yield materials exhibiting good physical properties and set times that were clinically acceptable.

What is claimed:

1. A curable dental composition comprising a preformed metal complex described by formula $$M(G)_g(F)_n \text{ or } M(G)_g(ZF_m)_n$$

where M is a group IIA, IIIA, IVA, transition metal, or inner transition metal element capable of forming a cationic species and having a valency of 2 or more; G is a multidentate organic chelating moiety capable of complexing with the element M to form a complexed metal having a four to eight membered ring structure; Z is hydrogen, boron, nitrogen, phosphorus, sulfur, antimony, or arsenic; F is associated with the completed metal as either a counterion or as a ligand; and g, m, and n are at least 1.

2. The composition of claim 1 wherein G is a multidentate organic chelating moiety selected from the group consisting of hydroxycarboxylic acids, melletic acids, polyglycols, β-diketones, β-ketoesters, aminocarboxylic acids, polyamines, aminoalcohols, aromatic heterocyclic bases, phenols, aminophenols, oximes, hydroxamic acids, Schiff bases, tetrapyrroles, sulfur compounds, synthetic macrocyclic compounds, phosphonic acids, polymeric compounds, and compounds having polymerizable groups.

3. The composition of claim 2 wherein the hydroxycarboxylic acids are selected from the group consisting of malic acid, tartaric acid, citric acid, hydroxybenzoic acids, hydroxytartaric acids, hydroxyethylethylenediaminetriacetic acid, N-hydroxyethylglycine, ethylenebis (hydroxyphenylglycine), gluconic acid, and 5-sulfosalicylic acid.

4. The composition of claim 2 wherein the aminocarboxylic acids are selected from the group consisting of ethylenediamine tetraacetic acid, hydroxyethylethylenediaminetriacetic acid, nitrilotriacetic acid, N-hydroxyethylglycine, and ethylenebis(hydroxyphenylglycine).

5. The composition of claim 2 wherein the polyamines are selected from the group consisting of ethylenediamine, triethylenetetramine, triaminotriethylamine, N-hydroxyethylenediamine, dipyridyl, o-phenanthroline, and polyethyleneimine.

6. The composition of claim 2 wherein the β-diketones are selected from the group consisting of acetylacetone, trifluoroacetylacetone, and thenoyltrifluoroacetone.

7. The composition of claim 2 wherein the aminoalcohols are selected from the group consisting of triethanolamine and N-hydroxyethylenediamine.

8. The composition of claim 2 wherein the aromatic heterocyclic bases are selected from the group consisting of dipyridyl and o-phenanthroline.

9. The composition of claim 2 wherein the phenols are selected from the group consisting of salicylaldehyde, disulfopyrocatechol, and chromotropic acid.

10. The composition of claim 2 wherein the aminophenols are selected from the group consisting of oxime, 8-hydroxyquinoline, and oxinesulfonic acid.

11. The composition of claim 2 wherein the oximes are selected from the group consisting of dimethylglyoxine and salicylaldoxime.

12. The composition of claim 2 wherein the Schiff bases are selected from the group consisting of disalicylaldehyde and 1,2-propylenedimine.

13. The composition of claim 2 wherein the tetrapyrroles are selected from the group consisting of tetraphenylporphin and phthalocyanine.

14. The composition of claim 2 wherein the sulfur compounds are selected from the group consisting of toluenedithiol, dimercaptopropanol, thioglycolic acid, potassium ethylxanthate, sodium diethyldithiocarbamate, dithizone, diethyl dithiophosphoric acid, and thiourea.

15. The composition of claim 2 wherein the polymeric compounds are selected from the group consisting of polyethyleneimine, polymethacryloylacetone, and poly(p-vinylbenzyliminodiacetic acid).

16. The composition of claim 2 wherein the phosphonic acids are selected from the group consisting of nitrilotrimethylenephosphonic acid, ethylenediaminetetra (methylenephosphonic acid), and hydroxyethylidenediphosphonic acid.

17. The composition of claim 2 wherein the compounds having polymerizable groups are selected from the group consisting of the following formulas:

-continued

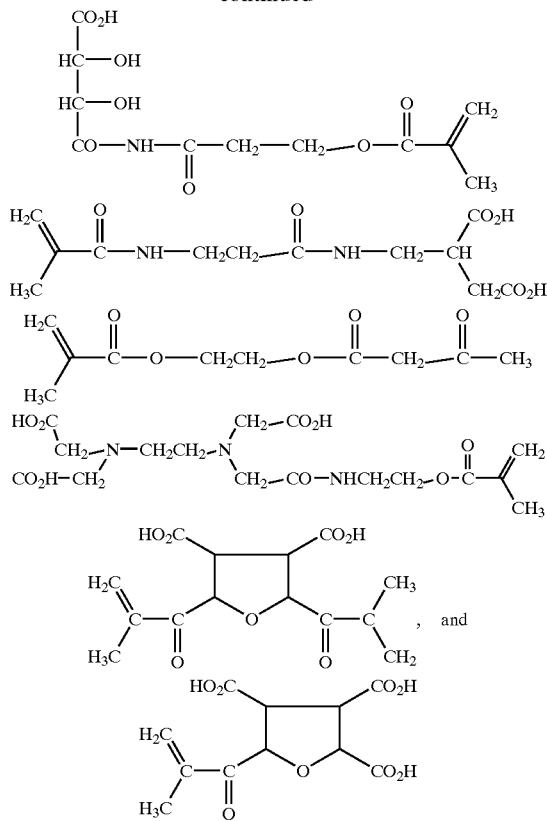

18. The composition of claim 1 wherein the curable dental composition is a one-part paste.

19. The composition of claim 1 wherein M is selected from the group consisting of $Ca^{+2}$, $Mg^{+2}$, $Sr^{+2}$, $Zn^{+2}$, $Al^{+3}$, $Zr^{+4}$, $Sn^{+2}$, $Yb^{+3}$, $Y^{+3}$ and $Sn^{+4}$.

20. The composition of claim 1 further comprising a fluoride-releasing fluoroaluminosilicate glass.

21. The composition of claim 1 wherein the composition is curable through a polymerization reaction.

22. The composition of claim 1 wherein the composition is curable through a setting reaction by virtue of a complexation reaction other than polymerization.

23. The composition of claim 1 wherein the composition is selected from the group consisting of zinc phosphate cements, polycarboxylate cements, glass ionomer cements, and dental amalgams.

24. The composition of claim 1 wherein the composition is curable through both a polymerization reaction and through a setting reaction by virtue of a complexation reaction other than polymerization.

25. A curable dental composition preparable by a method comprising:

providing a preformed metal complex; and incorporating the metal complex into the composition, wherein the metal complex is described by formula $$M(G)_g(F)_n \text{ or } M(G)_g(ZF_m)_n$$

where M is a group IIA, IIIA, IVA, transition metal, or inner transition metal element capable of forming a cationic species and having a valency of 2 or more; G is a multidentate organic chelating moiety capable of complexing with the element M to form a complexed metal having a four to eight membered ring structure; Z is hydrogen, boron, nitrogen, phosphorus, sulfur, antimony, or arsenic; F is associated with the complexed metal as either a counterion or as a ligand; and g, m, and n are at least 1.

26. A method for preparing a curable dental composition, the method comprising:

providing a preformed metal complex; and incorporating the metal complex into the composition, wherein the metal complex is described by formula $$M(G)_g(F)_n \text{ or } M(G)_g(ZF_m)_n$$

where M is a group IIA, IIIA, IVA, transition metal, or inner transition metal element capable of forming a cationic species and having a valency of 2 or more; G is a multidentate organic chelating moiety capable of complexing with the element M to form a complexed metal having a four to eight membered ring structure; Z is hydrogen, boron, nitrogen, phosphorus, sulfur, antimony, or arsenic; F is associated with the complexed metal as either a counterion or as a ligand; and g, m, and n are at least 1.

27. A curable dental composition comprising a preformed metal complex described by formula $$M(G)_g(F)_n \text{ or } M(G)_g(ZF_m)_n$$

where M is a group IIA, IIIA, IVA, transition metal, or inner transition metal element capable of forming a cationic species and having a valency of 2 or more; G is a multidentate organic chelating moiety selected from the group consisting of hydroxycarboxylic acids, melletic acids, polyglycols, β-diketones, β-ketoesters, aminocarboxylic acids, polyamines, aminoalcohols, aromatic heterocyclic bases, phenols, aminophenols, oximes, hydroxamic acids, Schiff bases, tetrapyrroles, sulfur compounds, synthetic macrocyclic compounds, phosphonic acids, polymeric compounds, and compounds having polymerizable groups; Z is hydrogen, boron, nitrogen, phosphorus, sulfur, antimony, or arsenic; F is associated with the complexed metal as either a counterion or as a ligand; and g, m, and n are at least 1.

* * * * *

UNITED STATES PATENT AND TRADEMARK OFFICE
CERTIFICATE OF CORRECTION

PATENT NO.    : 6,391,286 B1
DATED         : May 21, 2002
INVENTOR(S)   : Sumita B. Mitra and Bing Wang It is certified that error appears in the above-identified patent and that said Letters Patent is hereby corrected as shown below:

Column 2,
Line 36, please delete the word "arninocarboxylic" and insert in place thereof
-- aminocarboxylic --.

Column 21,
Line 5, please delete the word "ajar" and insert in place thereof -- a jar --.

Signed and Sealed this

Fourth Day of March, 2003

JAMES E. ROGAN
*Director of the United States Patent and Trademark Office*